(12) United States Patent
Telfair et al.

(10) Patent No.: US 7,771,417 B2
(45) Date of Patent: Aug. 10, 2010

(54) LASER SYSTEM WITH SHORT PULSE CHARACTERISTICS AND ITS METHODS OF USE

(75) Inventors: William Telfair, San Jose, CA (US); Ronald Avisa, Newark, CA (US); Stuart Mohr, Menlo Park, CA (US); David M. Buzawa, San Jose, CA (US)

(73) Assignee: IRIDEX Corporation, Mountain View, CA (US)

( * ) Notice: Subject to any disclaimer, the term of this patent is extended or adjusted under 35 U.S.C. 154(b) by 1386 days.

(21) Appl. No.: 11/066,615

(22) Filed: Feb. 24, 2005

(65) Prior Publication Data

US 2006/0187978 A1 Aug. 24, 2006

(51) Int. Cl.
*A61F 9/008* (2006.01)
(52) U.S. Cl. .................... 606/5; 606/4; 372/22; 372/75
(58) Field of Classification Search .................... 606/4, 606/5; 372/75, 22
See application file for complete search history.

(56) References Cited

U.S. PATENT DOCUMENTS

| | | | | |
|---|---|---|---|---|
| 4,885,471 A | * | 12/1989 | Telfair et al. | 250/461.1 |
| 4,916,319 A | * | 4/1990 | Telfair et al. | 250/461.1 |
| 5,302,259 A | * | 4/1994 | Birngruber | 250/526 |
| 5,549,596 A | | 8/1996 | Latina | |
| 5,556,395 A | * | 9/1996 | Shimmick et al. | 606/4 |
| 5,982,789 A | * | 11/1999 | Marshall et al. | 372/22 |
| 2001/0021205 A1 | | 9/2001 | Kittelmann et al. | |
| 2004/0039378 A1 | * | 2/2004 | Lin | 606/6 |
| 2004/0116909 A1 | * | 6/2004 | Neuberger et al. | 606/4 |
| 2006/0187978 A1 | * | 8/2006 | Telfair et al. | 372/25 |

FOREIGN PATENT DOCUMENTS

| | | |
|---|---|---|
| WO | WO 01/78830 A2 | 10/2001 |
| WO | WO 02/35353 A2 | 4/2002 |
| WO | WO 03/086322 A2 | 10/2003 |

OTHER PUBLICATIONS

Michail M. Pankratov, et al., "Pulsed Delivery of Laser Energy in Experimental Thermal Retinal Photocoagulation", SPIE, vol. 1202, pp. 205-213, (1990).
John Roider, et al., "Microphotocoagulation: Selective Effects of Repetitive Short Laser Pulses" Proceedings of the National Academy of Science, USA, vol. 90, pp. 8643-8647, (Sep. 1993).

(Continued)

*Primary Examiner*—Henry M Johnson, III
*Assistant Examiner*—Jeffrey B Lipitz
(74) *Attorney, Agent, or Firm*—Townsend and Townsend and Crew LLP

(57) ABSTRACT

A laser system that includes a diode pump source. A frequency doubled solid state visible laser is pumped by the diode pump source and produces a pulsed laser output with a train of pulses. Resources provide instructions for the creation of the pulsed output, with on and off times that provide for substantial confinement of thermal effects at a target site. This laser system results in tissue specific photoactivation (or TSP) without photocoagulation damage to any of the adjacent tissues and without causing full thickness retinal damage and the associated vision loss.

31 Claims, 1 Drawing Sheet

OTHER PUBLICATIONS

Johann Roider, et al., "Retinal Sparing by Selective Retinal Pigment Epithelial Photocoagulation", Archives of Opthalmology, vol. 117, pp. 1028-1034, (Aug. 1990).

Elias Reichecl, et al., "Transpupillary Thermotherapy of Occult Subfoveal Choroidal Neovascularization in Patients with Age-Related Macular Degeneration", Opthamology, vol. 106, pp. 1908-1914, (1999).

Martin A. Mainster, et al., "Transpupillary Thermotherapy for Age-Related Macular Degeneration: Long-Pulse Photocoagulation, Apoptosis, and Heat Shock Proteins", Ophthalmic Surg. Lasers, vol. 31, pp. 359-373, (2000).

Auge, et al., "Efficient CW and Q-switch operation of a self-frequency-doubling diode-pumped Nd: $Ca_4Gd_{1-x}Nd_xB_3O_{10}$ (Nd:GdCOB) Crystal.", Lasers and Electro-Optics, 1999, Summaries of papers presented at the conference on May 23-28, 1999.

Kiriyama, et al., Highly efficient thermal-birefringence-compensated-compensated laser-diode-pumped novel eight-pass Nd:YAG slab amplifier. Lasers and Electro-Optics, 1997.

Mitshke, et al., "Stabilizing the soliton laser", Quantum Electronics, IEEE Journal, vol. 22, Issue 12, pp. 2242-2250, (1986).

Supplemental European Search Report (Corresponding European Application No. EP 06735857) search completed Dec. 21, 2009 (4 pages total).

European Search Opinion of EP Patent Application No. 06735857.2, mailed May 27, 2010, 8 pages total.

* cited by examiner

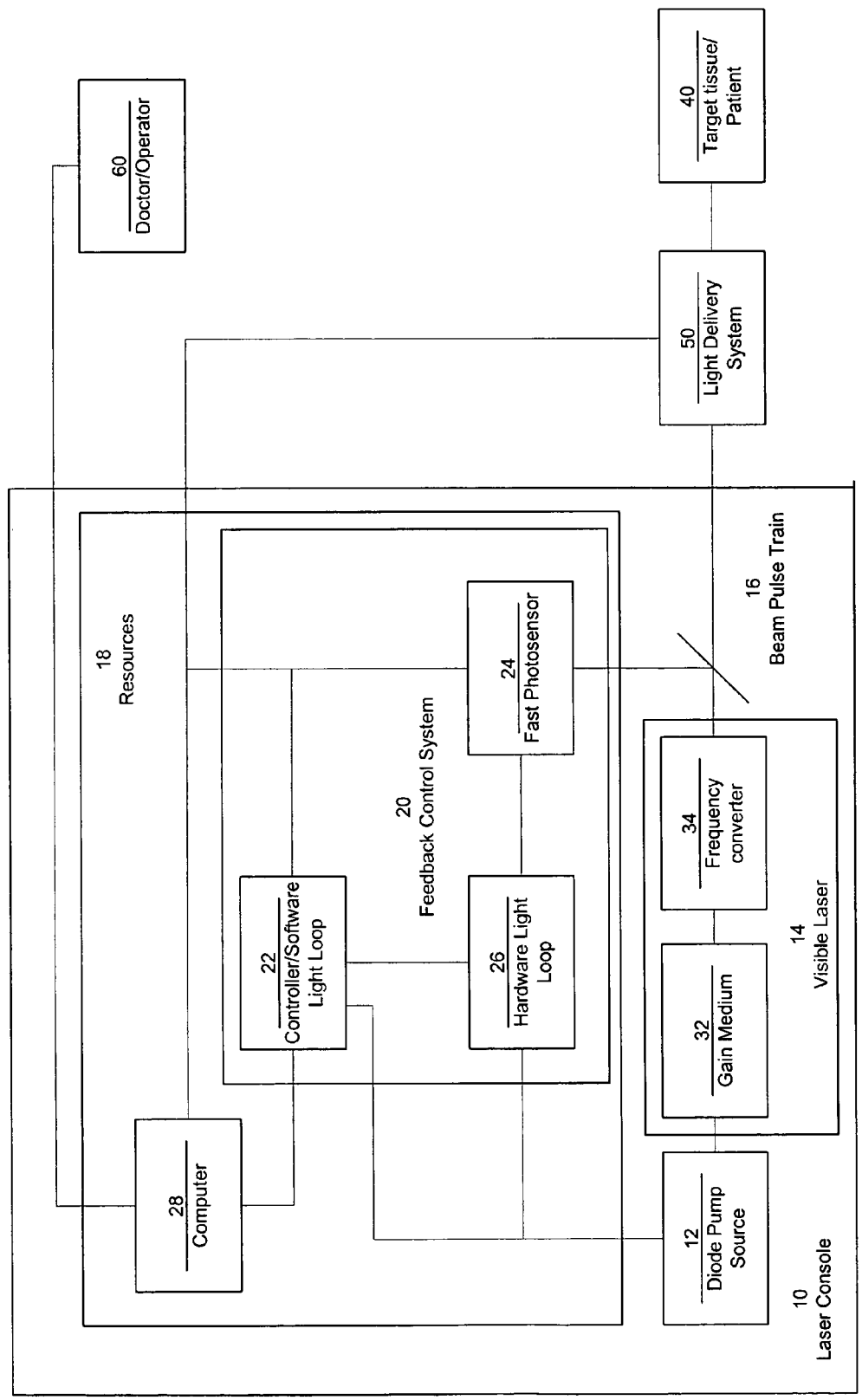
FIGURE 1. Block Diagram of the Invention

LASER SYSTEM WITH SHORT PULSE CHARACTERISTICS AND ITS METHODS OF USE

BACKGROUND OF THE INVENTION

1. Field of the Invention

This invention relates generally to laser systems, and their methods of use, that produce short and controlled pulse width trains, and more particularly to frequency doubled, cw laser systems, and their methods of use, that produce visible pulse trains of the appropriate pulselength, duty factor, and power to perform ophthalmology treatments currently being performed in the near-infrared.

2. Description of the Related Art

Laser photocoagulation (PC) is the current standard of care for the treatment of certain retinal diseases such as diabetic macular edema (DME), proliferative diabetic retinopathy (PDR), extrafoveal, juxtafoveal and some types of subfoveal retinal neovascularization (SRNV). The laser PC protocols validated by the diabetic retinopathy study (DRS), the early treatment of diabetic retinopathy study (ETDRS) and the macula photocoagulation study (MPS) all provide evidence for the beneficial use of lasers. Most of these treatments have been conducted with visible lasers (green and red lasers). All of these laser treatments are based upon obtaining a visible endpoint as the optimal tissue reaction, which becomes visible during the laser treatment. These laser pulsewidths are typically 50 to 300 milliseconds.

Current ophthalmic diode pumped solid state green lasers have pulsewidths of 10 to 60,000 milliseconds. This pulsewidth time domain is useful for the typical photothermal reactions normally requested in ocular Photocoagulation. In these applications the energy is absorbed by chromophores such as melanin or blood and conducts away from the absorbing or pigmented layers into adjacent non-absorbing and non-exposed layers—thus causing thermal damage laterally and axially into the clear layers in addition to the pigmented layers.

Microsecond short pulsed visible lasers have been demonstrated by Pankratov, "Pulsed delivery of laser energy in experimental thermal retinal photocoagulation", Proc. SPIE, V1202, pp. 205-213, 1990, Roider et. al., "Microphotocoagulation: Selective effects of repetitive short laser pulses", Proc. Natl. Acad. Sci, V90, pp 8643-8647, 1993, Roider et. al., "Retinal Sparing by Selective Retinal Pigment Epithelial Photocoagulation", Arch Ophthalmol, V117, pp 1028-1034, 1999, and U.S. Pat. No. 5,302,259 by Birngruber issued in 1994. These short pulse laser treatments have demonstrated beneficial effects while minimizing choroidal damage by using a pulse train with a low duty factor to confine the thermal effects to the absorbing layer or structure. Pankratov used an acousto-optical modulator to chop a continuous wave laser with pulse trains of 0.1 to 1.0 seconds and pulsewidths from 10 to 900 microseconds. However, the longer pulsewidths with high duty cycles behaved like CW. Only the shorter pulsewidths of 10 to 50 microseconds had beneficial effects of minimal to no visible lesions. The others used Q-switched green lasers with pulsewidths of 1.7 to 5 microseconds.

The Q-switched lasers have been used for certain thermal confinement applications such as selective laser trabeculoplasty (SLT) treatment for Glaucoma and selective retinal treatment (SRT) for clinically significant diabetic macular oedema (CSMO). In this case the energy is absorbed by the chromophores in such a short time that it cannot conduct away into adjacent tissue during the laser exposure time. The chromophore is heated to damaging levels and in certain cases will boil or explode—causing local mechanical damage in addition to the thermal damage to adjacent tissues. For these treatments, thermal confinement (or lack of thermal conduction) can only be achieved for pulses shorter than the time constant of the absorbing layer, which is on the order of 1 to 30 microseconds for the retinal pigment epithelium (RPE).

Pioneering studies using Near-InfraRed (NIR) diode lasers to treat retinal diseases without using the full energy of the traditional PC laser applications have been shown by Reichel et. al., "Transpupillary Thermotherapy of occult subfoveal choroidal neovascularization in patients with age-related macular degeneration", Ophthalmol, V106, pp 1908-1914, 1999 and by Mainster, et. al., "Transpupillary Thermotherapy: long-pulse photocoagulation, apoptosis and heat shock proteins", Ophthalmic Surg lasers, V31, pp 359-373, 2000. These laser treatments use energies below the threshold of visible tissue reaction. Procedures using these treatments are called Minimum Intensity Photocoagulation or MIP procedures. The lost of vision associated with the traditional PC treatments is mitigated due to the lower energies being used and thus not coagulating the retina photoreceptors in the neighboring clear layers.

There are two variations of these MIP treatments—one is called Transpupillary ThermoTherapy or TTT. This performs a long, CW, sub-threshold treatment—typically for 60 seconds—as described in the above references.

The other is a CW NIR laser with short and controlled pulse widths. It generates a pulse train of short pulses (typically 100 to 10,000 microseconds) with higher power during the pulse, but significant off time between pulses (typically 5 to 25% duty factor)—allowing the energy to be confined in a small volume using the Arrhenius principle. The thermal confinement results in tissue specific photoactivation because the specific absorbing tissue, which is being heated by the pulses to temperatures above the standard photocoagulation threshold, are activated but not coagulated, since the heat can dissipate fast enough that no coagulation takes place. This tissue specific photoactivation (or TSP) allows significant treatment without causing full thickness retinal damage and the associated vision loss.

The use of photoactivation in TSP instead of photocoagulation is meant to distinguish between these new subthreshold MIP treatments and the standard photocoagulation treatment. The standard treatment thermally heats the tissue until it starts to denature the protein structures and, hence, is called photocoagulation. This denaturization initiates a healing response, which ameliorates the disease.

The new MIP treatments heat the tissue and initiate some signal carrier cells, which initiate a healing response and this healing response ameliorates the disease being treated without coagulating any of the retinal layers and without the associated vision loss. Hence, activating the healing response without coagulating tissue and thus losing vision is a better treatment method.

Both of these treatments have been developed and are currently being used in many countries with Infrared lasers.

Physicians have not used green lasers for long sub-threshold treatments (like TTT) because of concerns regarding retinal phototoxicity. They have not used green lasers for pulse trains of short pulses, because current green lasers are unable to deliver similar pulse-width trains as those provided by the above referenced NIR laser with short and controlled pulse widths. By way of illustration, current green lasers employ a fast photodetector or photosensor to sense the output power level of the laser cavity. A software control light loop measures laser output on the millisecond time scale, and increases or decreases the requested energy by increasing or decreasing the requested drive current to the pump diode. This allows a relatively stable laser output, within a few percent, over long time periods such as pulses of tens to hundreds or even thousands of milliseconds.

In addition to the software light loop, a hardware light spike safety protection design has been used. This is an analog circuit that can respond to light energy changes in the microsecond regime. This is used to provide safety against a high power light spike, if some failure or current spike occurs. This protects the patient from spikes being delivered through the delivery system.

However, the hardware light loop threshold is generally set at 10 to 20% above the desired energy level, since it is a safety factor. There are numerous types of laser power fluctuations or changes that occur on this short time scale that can be smaller than this threshold or that bounce back and forth between transverse modes of the laser. These mode hops can cause power fluctuations of up to 10 to 20% before the hardware light loop kicks in. The software light loop is not able to respond to these quick changes and only make the fluctuations worse by trying to respond and varying the requested power.

There is a need to provide a system, and its methods of use, that can respond to these quick changes without making the fluctuations worse.

SUMMARY OF THE INVENTION

Accordingly, an object of the present invention is to provide an improved system, and its methods of use, that produces short and controlled pulse width trains.

Another object of the present invention is to provide a frequency doubled, cw laser system that produces short and controlled pulse width trains, and its methods of use, with reduced mode hops.

A further object of the present invention is to provide a frequency doubled, cw laser system that produces short and controlled pulse width trains, and its methods of use, with reduced power fluctuations.

Yet another object of the present invention is to provide a frequency doubled, cw laser system that produces short and controlled pulse width trains, and its methods of use, with power fluctuations less than 10%.

Still a further object of the present invention is to provide a frequency doubled, cw laser system, and its methods of use, that produces visible pulse trains of the appropriate pulselength, duty factor, and power to perform ophthalmology treatments currently being performed in the near-infrared.

Another object of the present invention is to provide a frequency doubled, cw laser system, and its methods of use, that deliver pulse rise times as short as 25 microseconds, pulselengths in the 25 microseconds to 10 milliseconds range, and pulse trains of these pulses for hundreds of pulses.

Yet another object of the present invention is to provide a frequency doubled, cw laser system, and its methods of use, suitable for treatment of the retina with a pulse train of visible pulses to cause change without coagulating the neurosensory elements of the retina.

These and other objects of the present invention are achieved in a laser system that includes a diode pump source. A frequency doubled solid state visible laser is pumped by the diode pump source and produces a pulsed laser output with a train of pulses. Resources provide instructions for the creation of the pulsed output, with on and off times that provide for substantial confinement of thermal effects at a target site.

In another embodiment of the present invention a method of treatment provides a diode pumped, frequency doubled solid state laser system. The solid state laser system produces a pulsed output that has a train of pulses with on times optimized for confinement of thermal effects. A plurality of pulses is directed to a target site. A temperature rise at the target site is non-additive from pulse to pulse.

In another embodiment of the present invention, a method is provided for treating biological tissue by laser surgery. A frequency doubled solid state visible laser system is provided that has a frequency doubler. Instructions are provided to the laser system to create a pulsed output that has a train of pulses with on and off times that substantially confine thermal effects. A pulsed output is produced and directed to a target site.

In another embodiment of the present invention, a laser treatment system includes a diode pump source that pumps a frequency doubled solid state visible laser. The frequency double solid state visible laser produces a pulsed output. A controller system is provided that is responsive to a photodetector. The controller system provides instructions to the visible laser to create the pulsed output. The pulsed output has a train of pulses with on and off times that substantially confine thermal effects.

BRIEF DESCRIPTION OF THE DRAWINGS

FIG. 1 is a schematic diagram of one embodiment of a frequency doubled, cw laser system of the present invention.

DETAILED DESCRIPTION OF THE EMBODIMENTS

In one embodiment of the present invention, illustrated in FIG. 1, a laser system 10 includes a diode pump source 12. A frequency doubled solid state visible laser 14 is pumped by the diode pump source 12 and produces a pulsed output 16 with a train of pulses. Resources 18 provide instructions for the creation of the pulsed output, with on and off times that provide for substantial confinement of thermal effects at a target site. An off time of the train of pulses is of sufficient duration to provide that the target site has sufficient time to cool down from the delivery of a previous pulse before a next pulse is delivered to the target site 40 by the delivery system 50.

In one embodiment, the resources 18, including a computer 28 to store input from a doctor/operator 60 and to calculate laser parameters, provide the correct parameters, and a trigger to the diode pump source 12, to provide for the pulsed output having the train of pulses with on times that are optimized for confinement of thermal effects. The instructions can include the following steps, set a starting current for the diode pump source 12, set a target power from the laser system 10, and trigger the diode pump source 12 to start. The resources 18 are configured to provide repetitive pulses at one target site. In one embodiment of the present invention, the resources 18 includes hardware and software components that work together to reduce uncertainty and fluctuation of energy down to the few percent range.

The resources 18 includes a feedback control system 20 which can include a controller 22 that is responsive to a device including but not limited to a photodetector 24. This feedback control system 20 has a software light loop as part of the controller 22 and a hardware light loop 26. The controller 22 produces a control signal used to adjust the pulsed output 16. The feedback control system 20 monitors the laser light delivered to the target site 40, and the pulsed output 16 is modified in response to the monitoring. In one embodiment, the train of pulses is optimized to confine the thermal effects of a target tissue 40 in a medical treatment.

In one embodiment, the controller 22 includes a processor that compares a signal, such as from the photodetector 24, to a target power and uses this comparison to determine the on and off times. The controller 22 can include a high speed circuit and/or a processor, that compares the signal, such as the signal from the photodetector 24, to a target power, and uses this comparison to determine the on and off time of each pulse.

The visible laser 14 has a gain medium 32. In various embodiments, the gain medium 32 can be made of a variety of materials, including but not limited to, Nd:YAG, Nd:YVO4, Nd:YLF, Ho:YAG, Er:YAG, Yb:YAG, Yb:YVO4, and the like.

The visible laser 14 also contains a frequency converter 34. In various embodiments, this frequency converter 34 can be made of a variety of materials, including but not limited to, KTP, LBO, BBO, and the like.

In one embodiment, the train of pulses has a thermal relaxation time less than a thermal relaxation time of the target site. In one embodiment of the present invention, the train of pulses have a pulse width that is less than 10 milliseconds. In another embodiment of the present invention, the train of pulses has pulses greater than 25 microseconds. In one specific embodiment, the train of pulses is optimized to confine the thermal effect to the RPE without affecting the neurosensory retina of the eye.

In one embodiment, the pulsed output 16 has a wavelength in the visible range suitable for a diode pumped solid state laser. The pulsed output 16 can have a pulse on time of 25 microseconds to 10,000 microseconds, a pulse off time of 75 to 100,000 microseconds, and the like.

In one embodiment of the present invention, each pulse length is controlled in the microsecond regime. In one embodiment of the present invention, the turn-on time of laser system 10 is less than 1 to 10 milliseconds. In one embodiment, the resources 18 with this new hardware/software combination light loop, the turn-on time can be decreased to 25 microseconds. The turn-off time is even shorter than the turn-on time. The control of total on-time can be implemented with a timer chip included with the resources, with sub-microsecond accuracy to time the pulse length and shut off the pulse at the appropriate time. In one embodiment of the present invention, micropulses of 25 up to 10,000 microseconds are provided by laser system 10 with power levels of up to 3 W. By way of illustration, and without limitation, pulse trains of up to 500 of these pulses with a variable duty factor from 5% to 25% are provided.

In one embodiment of the present invention, laser system 10 is utilized for a variety of different methods of treatment, particularly medical treatments. Suitable target, treatment sites 40 include but are not limited to, RPE, choriocapillaris and choroids of the eye, and the like. In this embodiment, laser system produces the pulsed output 16 with a train of pulses that have on times optimized for confinement of thermal effects to sites adjacent to the target site 40. A plurality of pulses is directed to the target site 40. A temperature rise at the target site 40 is non-additive from pulse to pulse. By way of illustration, and without limitation, the target site 40 can have an area of about 50 microns to 3 mm. In this method of treatment, the pulsed output has a wavelength range in the visible, and the pulsed output 16 can have a wavelength range of 520 to 615 nm.

EXAMPLE 1

In this example, the resources 18 have a hardware light loop threshold set at 3 to 5% above the desired power level. At the start of each pulse, the requested light level is set to maximum and held there until the laser power reaches the desired level. This generates the fastest possible rise time. When the laser power reaches the desired level, the resources 18 hold the power just above the desired level. The resources 18 then ramps the requested power level down until the laser power is equal to or below the desired level. If it is equal to or below the desired level, it steps back up slowly. If it is above, it steps down slowly. The resources 18 make a new measurement before each decision to raise or lower the requested level.

At this point the resources 18 requested level is close to the proper level and the combination of hardware and software keep the light within 3 to 5% as long as the pulse is on. The end result is a very fast turn on and stable light level throughout the entire pulse for each pulse of the pulsed output 16. The resources 18 makes a measurement before each decision to raise or lower the requested level, it can only be off of the correct level by one DAC number. The pulse energy stability for short pulses is improved.

EXAMPLE 2

In this example, laser system 10 is utilized to treat RPE, choriocapillaris and choroids of the eye. Pulsed output 16 is directed to target site 40 of the eye and a temperature rise at the target site is non-additive from pulse to pulse. The target site 40 is an area of 50 microns to 3 mm. The pulsed output 16 has a wavelength range of 520 to 615 nm. The pulsed output 16 has a pulse on time of 25 microseconds to 10,000 microseconds, and a pulse off time of 750 to 10,000 microseconds.

EXAMPLE 3

In this example, laser system 10 is utilized to treat RPE, choriocapillaris and choroids of the eye. The pulsed output 16 is directed to a target site of the eye and a temperature rise at the target site is non-additive from pulse to pulse. The target site 40 is an area of 50 microns to 3 mm. The controller 22 has a high speed circuit that compares a signal from the photodetector 24, to a target power, and uses this comparison to determine the on and off time of each pulse. The signal from photodetector 24 is compared to a target power to determine the on and off times.

The pulsed output 16 has a wavelength range of 520 to 615 nm. The pulsed output 16 has a pulse on time of 25 microseconds to 10,000 microseconds, and a pulse off time of 750 to 10,000 microseconds.

EXAMPLE 4

In this example, laser system 10 is utilized to treat RPE, choriocapillaris and choroids of the eye. The pulsed output 16 is directed to a target site of the eye and a temperature rise at the target site is non-additive from pulse to pulse. The target site 40 is an area of 50 microns to 3 mm. The train of pulses 16 is optimized to confine the thermal effect to the RPE target site without affecting the neurosensory retina of the eye. An off time of the train of pulses is of sufficient duration to provide that the RPE target site has sufficient time to cool down from a delivery of a previous pulse before a next pulse is delivered to the RPE target site.

The pulsed output 16 has a wavelength range of 520 to 615 nm. The pulsed output 16 has a pulse on time of 25 microseconds to 10,000 microseconds, and a pulse off time of 750 to 10,000 microseconds.

The foregoing description of embodiments of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A laser system, comprising:
   a diode pump source; and
   a frequency doubled solid state visible laser pumped by the diode pump source, the frequency double solid state visible laser producing an output of a train of pulses;
   a photodetector generating a signal; and
   a controller including a software control loop that, in response to the signal from the photodetector, alters drive current to the diode pump source within about a millisecond, and a hardware control loop that, in response to the signal from the photodetector, controls timing of the train of pulses to within a microsecond so that the controller provides instructions for the output of the train of pulses with on times of 25 microseconds to 10 milliseconds per pulse such that the train of pulses is sufficient for photoactivation of a therapeutic healing response in tissue at a target site, and off times of 75 to 100,000 microseconds such that the train of pulses is insufficient to induce traditional photocoagulation of the tissue at the target site, the photodetector coupling the controller to the pulsed output so that a power of the pulsed output is within less than 10% of a desired power.

2. The system of claim 1, wherein the train of pulses have a thermal relaxation time less than a thermal relaxation time of the target site.

3. The system of claim 1, wherein the train of pulses have a pulse width that is less than 10 milliseconds.

4. The system of claim 1, wherein the on and off times of the output of the train of pulses are modified in response to the monitoring.

5. The system of claim 1, wherein the controller produces a control signal, and wherein the control signal is used to adjust the power of the pulsed output by adjusting on and/or off times of the train of pulses so that the power of the pulsed output does not exceed a desired power by more than 5%.

6. The system of claim 1, wherein the train of pulses are optimized to confine the thermal effects of a target tissue in a medical treatment.

7. The system of claim 1, wherein the train of pulses are optimized to confine the thermal effect to the RPE without affecting the neurosensory retina of an eye.

8. The system of claim 1, wherein the off times of the train of pulses are of sufficient duration to provide that the target site has sufficient time to cool down from the delivery of a previous pulse before a next pulse is delivered to the target site so that a temperature rise at the target site is non-additive from pulse to pulse.

9. The system of claim 1, wherein the controller provides the correct parameters and a trigger to the diode pump source to provide for the pulsed output having the train of pulses with on times that are optimized for confinement of thermal effects.

10. The system of claim 1, wherein the software loop has instructions that include the following steps: set a starting current for the diode, set a target power from the laser, and trigger the diode to start.

11. The system of claim 1, wherein the resources are configured to provide repetitive pulses at one target site.

12. The system of claim 1, wherein the solid state laser has a gain medium selected from Nd:YAG, Nd:YVO4, Nd:YLF, Ho:YAG, Er:YAG, Yb:YAG, and Yb:YVO4.

13. A method of treatment, comprising: providing a diode pumped, frequency doubled solid state laser system with a pulsed output that has a train of pulses with on times of 25 microseconds to 10,000 microseconds, the on times optimized for confinement of thermal effects;
   directing the train of pulses from the laser system to a tissue at a target site;
   monitoring a power of the pulsed output using a photodetector coupled to a controller, the controller including a software control loop that, in response to a signal from the photodetector, alters drive current of the laser system within about a millisecond, and a hardware control loop that, in response to the signal from the photodetector, controls pulse timing to within a microsecond; and
   adjusting the pulsed output in response to the power by comparing the signal from the photodetector to a target power such that the power of the train of pulses is less than 10% of the target power and the train of pulses initiates a therapeutic healing response of the tissue at the target site, and such that the train of pulses is insufficient to effect traditional photocoagulation at the target site.

14. The method of claim 13, wherein the target site is selected from RPE, choriocapillaris and choroids of the eye.

15. The method of claim 13, wherein the target site has a spot size of about 50 microns to 3 mm.

16. The method of claim 13, wherein the pulsed output has a wavelength in the visible range.

17. The method of claim 13, wherein the pulsed output has a wavelength in a range of 520 to 615 nm.

18. The method of claim 13, wherein the pulsed output has a pulse off time of 750 to 10,000 microseconds such that a temperature rise at the target site is non-additive from pulse to pulse within the train of pulses.

19. A method of treating biological tissue by laser surgery, comprising:
   energizing a diode pumped, frequency doubled solid state laser system;
   controlling the laser system in response to feedback from a photodetector of the laser system with a controller, the controller including a software control loop that, in response to a signal from the photodetector, alters drive current of the laser system within about a millisecond, and a hardware control loop that, in response to the signal from the photodetector, controls pulse timing to within a microsecond so as to create an output of a train of pulses with on and off times that substantially confine thermal effects, wherein the train of pulses have a pulse width that is less than 10 milliseconds and greater than 25 microseconds; and
   directing the pulsed output wherein the controlling of the laser system is performed so that a power of the train of pulses is within less than 10% of a target power and is insufficient to effect traditional photocoagulation at the target site.

20. The method of claim 19, wherein the target site is selected from RPE, choriocapillaris and choroids of the eye.

21. The method of claim 19, wherein a temperature rise at the target site is non-additive from pulse to pulse.

22. The method of claim 19, further comprising:
utilizing the pulsed output to provide a non-ablative effect at the target site.

23. The method of claim 19, wherein the pulsed output is delivered to the target site until an integral of time and energy reaches an endpoint.

24. The method of claim 19, wherein the pulsed output is directed to the target site so as to heat at least one structure selected from RPE and choriocapillaris of the eye.

25. A laser treatment system, comprising:
a diode pump source coupled to a frequency doubled solid state visible laser pumped by the diode pump source, the frequency double solid state visible laser producing an output of a train of pulses with a power of within less than 10% of a desired output power;
a photodetector optically coupled to the laser; and
a controller responsive to a signal of the photodetector, the controller including a software control loop that, in response to the signal from the photodetector, alters drive current to the diode pump source within about a millisecond, and a hardware control loop that, in response to the signal from the photodetector, controls timing of the train of pulses to within a microsecond so that the controller provides instructions to the visible laser to create a pulsed output of the train of pulses with on and off in a range from about 25 microseconds to 10 milliseconds per pulse so as to substantially confine thermal effects of the train of pulses to be insufficient for traditional photocoagulation, and so as to induce a healing response.

26. The system of claim 25, wherein the hardware control loop of the controller comprises a high speed circuit that compares the photodetector signal to the target power and uses this comparison to determine the on and off time of each pulse.

27. The system of claim 25, wherein the hardware control loop of the controller comprises a high speed circuit and a processor that compares the photodetector signal to the target power and uses this comparison to determine the on and off times.

28. The system of claim 25, wherein the controller provides instructions for the creation of the pulsed output that has a train of pulses with on times of 10 to 900 microseconds and off times that provide for substantial confinement of thermal effects at a target site.

29. The system of claim 25, wherein the controller provides instructions for the creation of the pulsed output that has a train of pulses such that the train of pulses is sufficient to effect photoactivation of tissue at a target site, and off times such that the train of pulses is insufficient to induce traditional photocoagulation of the tissue at the target site when the target site is selected from RPE, choriocapillaris and choroids of an eye.

30. The system of claim 1, wherein the software loop of the controller is configured so that the train of pulses directed at the target site is limited to a range of from 2 to 500 pulses.

31. The method of claim 13, further comprising limiting the train of pulses directed at the target site to a range of from 2 to 500 pulses with the controller.

* * * * *